(12) United States Patent
Baillet

(10) Patent No.: US 8,739,782 B2
(45) Date of Patent: Jun. 3, 2014

(54) POWDER INHALATION DEVICE

(75) Inventor: Matthieu Baillet, Bonsecours (FR)

(73) Assignee: Aptar France SAS, Le Neubourg (FR)

( * ) Notice: Subject to any disclaimer, the term of this patent is extended or adjusted under 35 U.S.C. 154(b) by 199 days.

(21) Appl. No.: 13/061,357

(22) PCT Filed: Sep. 29, 2009

(86) PCT No.: PCT/FR2009/051848
§ 371 (c)(1),
(2), (4) Date: Feb. 28, 2011

(87) PCT Pub. No.: WO2010/037965
PCT Pub. Date: Apr. 8, 2010

(65) Prior Publication Data
US 2011/0168178 A1    Jul. 14, 2011

(30) Foreign Application Priority Data

Sep. 30, 2008 (FR) ...................................... 08 56561

(51) Int. Cl.
*A61M 15/00* (2006.01)
(52) U.S. Cl.
USPC .................................................. 128/203.15
(58) Field of Classification Search
USPC ............ 128/203.15, 200.23, 200.24, 203.12, 128/205.23, 203.21; 222/36, 38, 41, 222/153.13, 129, 394, 80, 81, 402.2
See application file for complete search history.

(56) References Cited

U.S. PATENT DOCUMENTS

| | | | |
|---|---|---|---|
| 5,469,843 A | 11/1995 | Hodson | |
| 6,715,486 B2 | 4/2004 | Gieschen et al. | |
| 8,261,740 B2 * | 9/2012 | Pocock et al. | ........... 128/203.15 |
| 2008/0099015 A1 | 5/2008 | Pocock et al. | |
| 2008/0142009 A1 | 6/2008 | Carrico et al. | |

FOREIGN PATENT DOCUMENTS

| | | |
|---|---|---|
| EP | 1 905 470 A2 | 4/2008 |
| FR | 2 881 117 A1 | 7/2006 |
| FR | 2 909 641 A1 | 6/2008 |
| WO | 01/26720 A1 | 4/2001 |
| WO | 2007/118490 A1 | 10/2007 |
| WO | WO 2008012458 A2 * | 1/2008 |

OTHER PUBLICATIONS

International Preliminary Report on Patentability issued on Sep. 29, 2009 for counterpart application PCT/FR2009/051848.

* cited by examiner

*Primary Examiner* — Jackie Ho
*Assistant Examiner* — Mark Wardas
(74) *Attorney, Agent, or Firm* — Sughrue Mion, PLLC

(57) ABSTRACT

A powder inhaler comprising: a body that is provided with a dispenser orifice; a plurality of reservoirs each containing a dose of powder; a perforator to perforate a predosed reservoir on each actuation; and a dispersion channel including an inlet that is connected to the perforator and that receives the dose of powder from the reservoir, and an outlet connected to the dispenser orifice, the perforator controlled by inhalation, the dispersion channel including two bent channel portions, a first bent channel portion that is connected to said inlet via a first substantially-rectilinear channel portion, and a second bent channel portion connected to the outlet via a second substantially-rectilinear channel portion, the two bent channel portions being interconnected via a third substantially-rectilinear channel portion, the cross-section of the third substantially-rectilinear channel portion being smaller than the cross-section of the first substantially-rectilinear channel portion.

18 Claims, 2 Drawing Sheets

POWDER INHALATION DEVICE

CROSS REFERENCE TO RELATED APPLICATION

This application is a National Stage of International Application No. PCT/FR2009/051848 filed Sep. 29, 2009, claiming priority based on French Patent Application No. 08 56561, filed Sep. 30, 2008, the contents of all of which are incorporated herein by reference in their entirety.

The present invention relates to a powder inhaler, and more particularly to a dry-powder inhaler.

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. However, the inhaler is more difficult to use, since the user is obliged to load a capsule into the inhaler before each use. Another type of inhaler consists in packaging the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of metering accuracy and reproducibility on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the previous dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation.

In order to dispense the powder in a finely pulverized form, document U.S. Pat. No. 6,715,486 describes a dispersion chamber containing one or more balls that are driven in rotation by the flow of air and powder directed from the open reservoir towards the dispenser orifice. The dispersion chamber breaks up clumps of the powder in satisfactory manner, and has a positive effect on flow resistance by reducing it. However, the effects of the ball-containing chamber are relatively sensitive to the orientation of the inhaler during inhalation, with properties of yield, variability, or resistance possibly being affected in the event of non-optimum orientation, corresponding to the inhaler being held other than vertically. In addition, the use of balls complicates assembly and makes it more costly.

Documents WO 01/26720, FR-2 881 1 17, FR-2 909 641, WO 2007/1 18490, and U.S. Pat. No. 5,469,843 describe prior-art devices.

An object of the present invention is to provide a fluid dispenser device, in particular a dry-powder inhaler, that does not have the above-mentioned drawbacks.

In particular, an object of the present invention is to provide such an inhaler that is simple and inexpensive to manufacture and to assemble, that is reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

Another object of the present invention is to provide such an inhaler that guarantees good metering accuracy and good metering reproducibility on each actuation, regardless of the orientation of the inhaler.

The present invention thus provides a powder inhaler comprising: a body that is provided with a dispenser orifice; a plurality of predosed reservoirs each containing a dose of powder for dispensing; and reservoir-opening means for opening a reservoir on each actuation, said opening means being perforator means comprising a needle that is adapted to perforate a predosed reservoir on each actuation; the inhaler further comprising a dispersion channel including an inlet that is connected to said perforator means and that receives the dose of powder from said open reservoir, and an outlet that is connected to said dispenser orifice, said perforator means being controlled by the user inhaling, such that a predosed reservoir is simultaneously perforated and emptied, the powder driven by the inhalation flow passing through said dispersion channel before being expelled through the dispenser orifice, said dispersion channel including two bent channel portions, a first bent channel portion that is connected to said inlet via a first substantially-rectilinear channel portion, and a second bent channel portion that is connected to said outlet via a second substantially-rectilinear channel portion, said two bent channel portions being interconnected via a third substantially-rectilinear channel portion, the cross-section of said third substantially-rectilinear channel portion being smaller than the cross-section of said first substantially-rectilinear channel portion.

Advantageously, said first and second substantially-rectilinear channel portions are substantially parallel.

Advantageously, said first bent channel portion forms an angle that is greater than or equal to 90°, preferably about 100°.

Advantageously, said second bent channel portion forms an angle that is greater than or equal to 90°, preferably about 100°.

Advantageously, said dispersion channel comprises a base portion and a cover portion.

Advantageously, the inlet and the first substantially-rectilinear channel portion of the dispersion channel are formed on the base portion, the outlet and the second substantially-rectilinear channel portion are formed on the cover portion, and said two bent channel portions and said third substantially-rectilinear channel portion are formed both on the base portion and on the cover portion.

Advantageously, said first substantially-rectilinear channel portion and/or said second substantially-rectilinear channel portion and/or said third substantially-rectilinear channel portion have cross-sections that are substantially constant along their respective lengths.

Advantageously, said second substantially-rectilinear channel portion includes constriction means.

These characteristics and advantages and others of the present invention appear more clearly from the following detailed description, given by way of non-limiting example, and with reference to the accompanying drawings, and in which.

Figure 1:
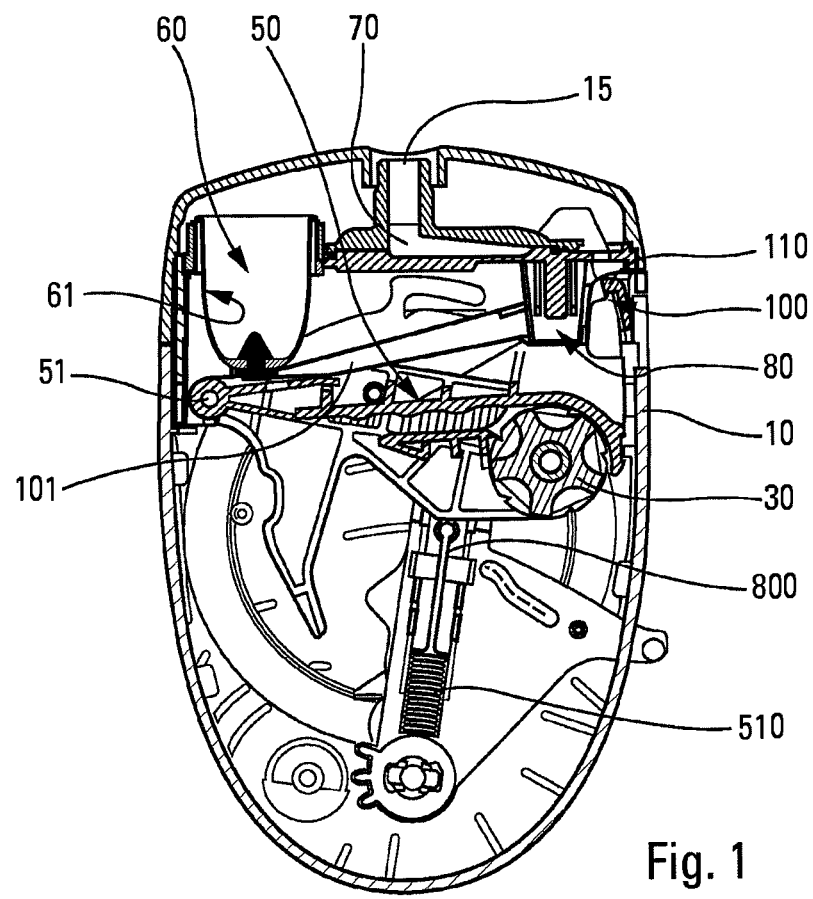
FIG. 1 is a diagrammatic section view of a powder inhaler.

FIG. 1 shows an advantageous variant embodiment of a dry-powder inhaler. The inhaler includes a body 10 on which there can be slidably or pivotally mounted two cap-forming portions (not shown) that are adapted to be opened so as to open and pre-stress the device. The body 10 can be approximately rounded in shape, but it could be of any other appropriate shape. The body 10 includes a mouthpiece or inhaler endpiece that defines a dispenser orifice 15 through which the user inhales while the device is being actuated. The caps can be opened by pivoting about a common pivot axis, but any other opening means can be envisaged for opening the device. In a variant, the device could include a single cover instead of two.

Inside the body 10 there is provided a strip (not shown) of individual predosed reservoirs, also known as blisters, said strip being made in the form of a flexible elongate strip on which the blisters are disposed one behind another, in manner known per se. Before first use, the blister strip can be rolled-up inside the body 10, preferably in a storage portion, and first displacement means for displacing the strip 30 are provided for progressively unrolling the blister strip and for causing it to advance. Second displacement means 50, 51 are provided for bringing a respective blister or individual reservoir into a dispensing position each time the device is actuated. The strip portion including the empty reservoirs is advantageously adapted to be rolled-up at another location of said body 10, preferably a reception portion.

The inhaler includes reservoir opening means 80 (that are shown only in very diagrammatic manner in FIG. 1, but that can be seen better in FIGS. 2 and 4) preferably comprising perforator and/or cutter means for perforating and/or cutting the closure layer of the blisters. For example, the reservoir opening means advantageously comprise a needle that is preferably stationary relative to the body 10, and against which a respective blister is displaced on each actuation by the second displacement means. The blister is thus perforated by said needle which penetrates into said blister so as to expel the powder by means of the suction of the user inhaling.

The first displacement means are adapted to cause the blister strip to advance before and/or during and/or after each actuation of the device. The second displacement means are adapted to displace the reservoir to be emptied against said perforator and/or cutter means during actuation. The second displacement means can be urged, via stressing means 800, by a resilient element 510, such as a spring or any other equivalent resilient element, said resilient element being suitable for being pre-stressed while the device is being opened. The first displacement means preferably comprise an indexer wheel 30 that receives and guides the blisters. Turning the indexer wheel causes the blister strip to advance. In a particular angular position, a given reservoir is always in a position facing the opening means. The second displacement means can include a rotary support element 50 that turns about an axis of rotation 51, said indexer wheel 30 being rotatably mounted on said support element.

An actuation cycle of the device can be as follows. While the device is being opened, the two cap-forming lateral portions are moved apart by pivoting on the body in order to open the device and thus pre-stress the device. In this position, the indexer wheel cannot be displaced towards the needle, since the second displacement means are held by appropriate blocking means 100, 110. Preferably, it is while the user is inhaling through the mouthpiece that the blocking means are unblocked, thereby causing said support element 50 to pivot and thus said indexer wheel 30 to move towards the needle, and thereby causing a reservoir to be opened.

In use, the optimum orientation of the inhaler corresponds to a position that is substantially vertical, with the dispenser orifice 15 directed upwards, as shown in FIG. 1. Nevertheless, the inhaler of the present invention can be used in any position.

As explained above, it is desirable for the opening means to be actuated by the user inhaling. In order to trigger the reservoir opening means by inhalation, an inhalation trigger system can be provided that advantageously comprises a unit 60 that is displaceable and/or deformable under the effect of inhalation, the unit being adapted to release the blocking means 100, 110, e.g. via a rod 101. The unit advantageously comprises a deformable air-chamber 61. Inhalation by the user causes said deformable air-chamber to deform, thereby making it possible to release said blocking means and to enable the displacement of the second displacement means, and therefore of a respective reservoir towards its opening position. The reservoir is therefore opened only on inhalation, such that it is emptied simultaneously. Thus, there is no risk of any of the dose being lost between opening the reservoir and emptying it.

In a variant, other inhalation trigger means could also be used, e.g. using a pivotable valve flap that, while the user is inhaling, pivots under the effect of the suction created by the inhalation, with pivoting of the valve flap causing the blocking means blocking the movable support means to be released, thereby causing the reservoir to be displaced towards the opening means.

After inhalation, when the user closes the device, all of the components return to their initial, rest position. The device is thus ready for a new utilization cycle.

In the invention, the inhaler includes a dispersion channel 70 for receiving the dose of powder after a respective reservoir has been opened. The dispersion channel 70 includes an inlet 710 that is directly connected to the reservoir opening means, and an outlet 720 that is directly connected to the dispenser orifice 15. Thus, no dispersion chamber, with or without balls, is provided between the inlet 710 and the outlet 720 of said dispersion channel 70, and thus between the perforator means 80 and the dispenser orifice 15. This implementation thus simplifies the manufacture and the assembly of the device.

Figure 2:
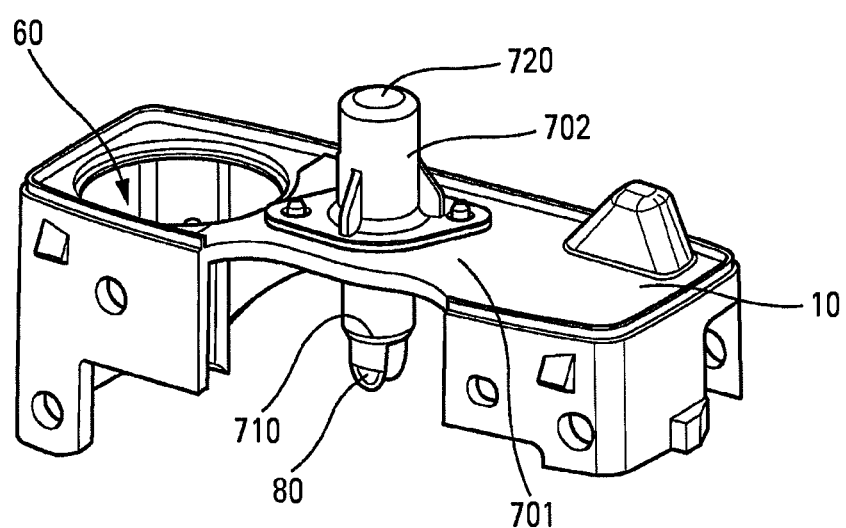
FIG. 2 is an exploded diagrammatic perspective view of a portion of the inhaler in a variant embodiment.

The embodiment in FIG. 2 shows a substantially-rectilinear channel between the inlet 710 and the outlet 720 of the channel. Advantageously, the cross-section of the dispersion channel 70 is substantially constant along the entire length of said channel.

Figure 3:
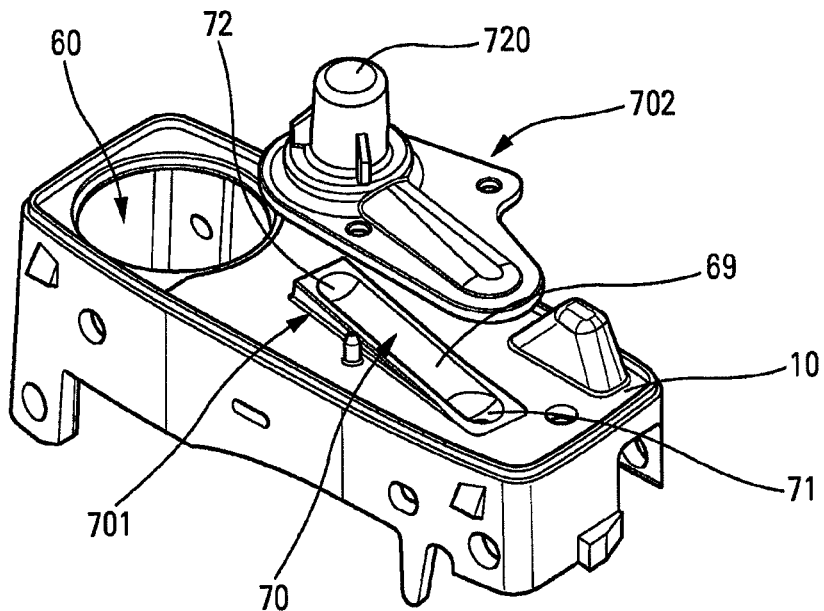
FIG. 3 is a view similar to the view in FIG. 2, showing an advantageous embodiment of the invention.
Figure 4:
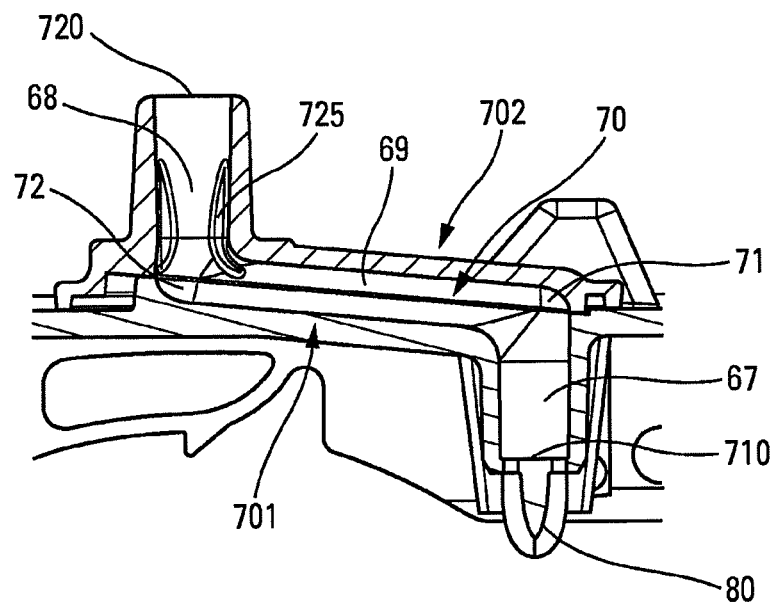
FIG. 4 is a diagrammatic side section view of the portion of the FIG. 3 inhaler.

The dispersion channel 70 includes at least one first bent channel portion 71 that is connected to said inlet 710 via a first substantially-rectilinear channel portion 67, preferably of constant cross-section along its length. Advantageously, the dispersion channel 70 also includes a second bent channel portion 72 that is connected to said outlet 720 via a first substantially-rectilinear channel portion 68 that may also be of constant cross-section. FIGS. 1, 3, and 4 show examples of these two bent channel portions. The two bent channel portions 71 and 72 may be interconnected via a third substantially-rectilinear channel portion 69 that is preferably also of constant cross-section. In the invention, the third substantially-rectilinear channel portion 69 has a cross-section that is smaller than the cross-section of the first substantially-rectilinear channel portion 67, resulting in the flow of air and powder that passes therethrough accelerating. In a variant, as shown very diagrammatically in FIG. 1, the third substantially-rectilinear channel portion 69 could equally well have a cross-section that increases towards the second bent channel portion 72. The second substantially-rectilinear channel portion 68 may have a cross-section that is similar to the cross-section of the first substantially-rectilinear channel portion 67, as can be seen in FIG. 4. It may also include constriction means 725, e.g. one or more inwardly-projecting projections, so as to disrupt the flow of air and powder and so as to encourage said powder to break up. The dimensions and sections of the various channel portions may be optimized as a function of the arrangement of the different component parts of the inhaler, and as a function of the desired performance.

Advantageously, the angle formed by the two bent portions 71 and 72 is greater than or equal to 90°, preferably about 100°. As can be seen in FIGS. 3 and 4, the first and second substantially-rectilinear channel portions 67 and 68 may be substantially parallel, and the third substantially-rectilinear channel portion 69 may slope a little between the two bent channel portions 71 and 72. This produces excellent yields, with more than 95% of the powder initially contained in a reservoir being transmitted to the outlet 720 of said dispersion channel 70. In addition, very good metering reproducibility is obtained during successive actuations. Naturally, the dimensions and orientations of the various channel portions may be optimized depending on the features of the inhaler, so as to maximize the performance thereof.

Advantageously, the dispersion channel 70 comprises a base portion 701 and a cover portion 702. Preferably, as can be seen in FIGS. 3 and 4, the inlet 710 and the first rectilinear channel portion 67 are formed exclusively on the base portion 701. Likewise, the outlet 720 and the second substantially-rectilinear channel portion 68 are preferably formed exclusively on the cover portion 702. The two bent channel portions 71 and 72, and the third substantially-rectilinear channel portion 69, are preferably formed on both the base and cover portions. This simplifies by molding and assembly.

The present invention therefore makes it possible to provide a dry-powder inhaler that performs the following functions:

- a plurality of individual doses of powder stored in individual sealed reservoirs, e.g. 30 or 60 doses stored on a rolled-up strip;
- the powder is released by perforation that is achieved by the user inhaling, the blister being perforated by means of an inhalation detector system that is coupled to a pre-stressed release system;
- appropriately-shaped drive means that are engaged with blisters so as to displace the blister strip on each actuation, and to bring a new reservoir into a position in which it is to be opened by appropriate opening means;
- an effective dispersion of the powder prior to it being expelled, so as to limit the amount of powder that is retained, and so as to guarantee good metering accuracy and reproducibility on each actuation, even when the orientation of the inhalation is not optimum.

Other functions are also provided by the device of the invention as described above. It should be observed that the various functions, even if they are shown as being provided simultaneously on the embodiments of the inhaler, could be implemented separately. In particular, the inhalation trigger mechanism could be used regardless of the type of reservoir opening means, regardless of the use of a dose indicator, regardless of the way in which the individual reservoirs are arranged relative to one another, regardless of the shape of the dispersion channel, etc. The cocking means and the inhalation trigger system could be made in some other way. The same applies for other component parts of the device.

Various modifications can also be envisaged by a person skilled in the art, without going beyond the ambit of the present invention, as defined by the accompanying claims.

The invention claimed is:

1. A powder inhaler comprising: a body (10) that is provided with a dispenser orifice (15); a plurality of predosed reservoirs each containing a dose of powder for dispensing; and reservoir-opening means (80) for opening a reservoir on each actuation, said opening means being perforator means comprising a needle that is adapted to perforate a predosed reservoir on each actuation; the inhaler further comprising a dispersion channel (70) including an inlet (710) that is connected to said perforator means (80) and that receives the dose of powder from said open reservoir, and an outlet (720) that is connected to said dispenser orifice (15), said perforator means being controlled by the user inhaling, such that a predosed reservoir is simultaneously perforated and emptied, the powder driven by the inhalation flow passing through said dispersion channel before being expelled through the dispenser orifice, the inhaler being characterized in that said dispersion channel (70) includes two bent channel portions (71, 72), a first bent channel portion (71) that is directly connected to said inlet (710) via a first substantially-rectilinear channel portion (67), and a second bent channel portion (72) that is directly connected to said outlet (720) via a second substantially-rectilinear channel portion (68), said two bent channel portions (71, 72) being directly interconnected via a third substantially-rectilinear channel portion (69) that extends the entire distance between the first bent channel portion and the second bent channel portion, the cross-section of said third substantially-rectilinear channel portion (69) being smaller than the cross-section of said first substantially-rectilinear channel portion (67).

2. An inhaler according to claim 1, wherein said first and second substantially-rectilinear channel portions (67, 68) are substantially parallel.

3. An inhaler according to claim 1, wherein said first bent channel portion forms an angle that is greater than or equal to 90°.

4. An inhaler according to claim 1, wherein said second bent channel portion forms an angle that is greater than or equal to 90°.

5. An inhaler according to claim 1, wherein said dispersion channel (70) comprises a base portion (701) and a cover portion (702).

6. An inhaler according to claim 5, wherein the inlet (710) and the first substantially-rectilinear channel portion (67) of the dispersion channel (70) are formed on the base portion (701), the outlet (720) and the second substantially-rectilinear channel portion (68) are formed on the cover portion (702), and said two bent channel portions (71, 72) and said third substantially-rectilinear channel portion (69) are formed both on the base portion (701) and on the cover portion (702).

7. An inhaler according to claim 1, wherein at least one of said first substantially-rectilinear channel portion (67), said second substantially-rectilinear channel portion (68) and said third substantially-rectilinear channel portion (69) has a cross-section that is substantially constant along its respective length.

8. An inhaler according to claim 1, wherein said second substantially-rectilinear channel portion (68) includes constriction means (725).

9. The inhaler according to claim 1, wherein said first bent channel portion forms an angle that is greater than or equal to 100°.

10. The inhaler according to claim 1, wherein said second bent channel portion forms an angle that is greater than or equal to 100°.

11. A powder inhaler comprising:
a body provided with a dispenser orifice;
a plurality of predosed reservoirs, each containing a dose of powder for dispensing; and
a perforator configured to open in turn each of the reservoirs of the plurality of predosed reservoirs on each actuation;
a dispersion channel including an inlet connected to the perforator and configured to receive the dose of powder from each opened reservoir, and an outlet connected to the dispenser orifice, the perforator controlled by inhalation such that a predosed reservoir in turn for opening is simultaneously perforated and emptied, the powder driven by the inhalation flow passing through the dispersion channel before being expelled through the dispenser orifice;
wherein the dispersion channel comprises two bends, a first bend connected at one end to the inlet via a first rectilinear channel portion having a first longitudinal axis, and a second bend connected at one end to the outlet via a second rectilinear channel portion having a second longitudinal axis, the two bends are interconnected via a third rectilinear channel portion having a third longitudinal axis, a cross-sectional area of the third rectilinear channel portion taken in a direction orthogonal to the third longitudinal axis is smaller than a cross-sectional area of the first rectilinear channel portion taken in a direction orthogonal to the first longitudinal axis so as to accelerate flow of air through the third rectilinear channel portion; and wherein the first rectilinear channel portion is directly coupled to the first bend, the second rectilinear channel portion is directly coupled to the second bend, and the third rectilinear channel is directly coupled to the first bend and to the second bend.

12. The powder inhaler according to claim 11, wherein at least one of the first rectilinear channel portion, the said second rectilinear channel portion and the third rectilinear channel portion has a substantially constant cross-section, taken in a direction orthogonal to the corresponding longitudinal axis, along an entire or substantially the entire length of the corresponding channel portion.

13. The powder inhaler according to claim 11, wherein each of the first rectilinear channel portion, the said second rectilinear channel portion and the third rectilinear channel portion has a constant cross-section, taken in a direction orthogonal to the corresponding longitudinal axis, along an entire or substantially the entire length of the corresponding channel portion.

14. The powder inhaler according to claim 11, wherein the first and second rectilinear channel portions are substantially parallel to each other.

15. The powder inhaler according to claim 11, wherein the first bend forms an angle that is greater than or equal to 90°.

16. The powder inhaler according to claim 11, wherein the second bend forms an angle that is greater than or equal to 90°.

17. The powder inhaler according to claim 11, wherein the second rectilinear channel portion comprises a constriction.

18. The powder inhaler according to claim 17, wherein the constriction comprises one or more inwardly-projecting projections configured to disrupt flow of air and powder and assist in breaking up the powder.

* * * * *